United States Patent [19]

DeVillez et al.

[11] Patent Number: 4,927,626

[45] Date of Patent: May 22, 1990

[54] METHOD FOR ENHANCEMENT OF UNGUIS GROWTH

[76] Inventors: Richard L. DeVillez, 930 Forrest Dr., Kalamazoo, Mich. 49002; Richard K. Scher, 913 Gardiner Dr., P.O. Box P107, Bay Shore, N.Y. 11706

[21] Appl. No.: 264,470

[22] Filed: Oct. 28, 1988

[51] Int. Cl.$^5$ .......................... A61K 7/04; A61K 9/12
[52] U.S. Cl. ......................................... 424/61; 424/47
[58] Field of Search ........................... 514/946; 424/61

[56] References Cited

U.S. PATENT DOCUMENTS

| | | | |
|---|---|---|---|
| 3,382,247 | 5/1968 | Anthony et al. | 260/256.4 |
| 3,461,461 | 8/1969 | Anthony et al. | 260/256.4 |
| 3,644,364 | 2/1972 | Anthony | 260/256.4 |
| 4,139,619 | 2/1979 | Chidsey | 424/45 |
| 4,287,338 | 9/1981 | McCall | 544/123 |
| 4,596,812 | 6/1986 | Chidsey et al. | 514/256 |
| 4,631,186 | 12/1986 | Brown | 424/61 |
| 4,746,675 | 5/1988 | Makino et al. | 514/946 |
| 4,808,414 | 2/1989 | Peck et al. | 514/946 |

FOREIGN PATENT DOCUMENTS

| | | | |
|---|---|---|---|
| 0228423 | 11/1985 | Japan | 514/946 |
| 1255640 | 12/1971 | United Kingdom | 424/61 |
| 2114580 | 8/1983 | United Kingdom | 424/61 |

OTHER PUBLICATIONS

J. M. McCall et al., "A New Approach to Triaminopyrimidine N-Oxides", Journal of Organic Chemistry, vol. 40, No. 22, pp. 3304–3306, (1975).

*Primary Examiner*—Dale R. Ore
*Attorney, Agent, or Firm*—Donald L. Corneglio

[57] ABSTRACT

A method for enhancing the growth of unguis in animals including humans comprising the topical application of minoxidil to the growth region of the unguis. The method is useful in the treatment of nails, hoofs, claws and talons to enhance their growth for medical or cosmetic purposes.

5 Claims, No Drawings

METHOD FOR ENHANCEMENT OF UNGUIS GROWTH

BACKGROUND OF THE INVENTION

The present invention is a method for enhancing the growth of unguis in animals, including humans. In humans, unguis is the horny cutaneous plate on the dorsal surface of the distal end of the terminal phalanx of a finger or toe, i.e., fingernail or toenail. In horses and other ungulate, dogs or birds this horny cutaneous plate is known as the hoof, claw or talon, respectively. In all animals the unguis is made up of flattened epithelial scales developed from specialized epithelial cells called the matrix.

In all animals the unguis is exposed to abrasive and sometimes destructive forces which make it desirable to be able to influence or treat its growth rate, thickness, brittleness and strength. This is especially true for hoofs of animals and the fingernails of humans. In other situations it is desirable to influence the growth of unguis for cosmetic purposes which is especially true for humans and animals bred for show purposes.

The unguis is also prone to infections and diseases which sometimes necessitate its total or partial removal and therefore it is desirable to regrow the unguis as fast as possible to restore normal function. Heretofor, there has been no known scientific treatment for medically or cosmetically influencing the growth of unguis in humans. Some substances are available for treatment of horse hoofs; however, more desirable and effective treatments are sought. Therefore, the present method is a significant advancement in the field for medical, veterinarian and cosmetic use.

INFORMATION DISCLOSURE

Topical compositions of minoxidil are known for treatment of baldness and are disclosed in U.S. Pat. Nos. 4,139,619 and 4,596,812. Also, various salts and derivatives of minoxidil, as well as associated methods, are known and disclosed in U.S. Pat. Nos. 3,382,247, 3,461,461, 3,644,364 and 4,287,338 and published by J. M. McCall, et al., Journal of Organic Chemistry, 40, 3304 (1975).

SUMMARY OF THE INVENTION

In one aspect the subject invention is a method for enhancing the growth of unguis in animals, including humans, comprising the topical application of an effective amount of minoxidil to a region of the unguis where it emerges from the skin. Typically, the region where the unguis emerges from the skin is the growth region (a specialized epithelial invagination called the matrix).

Generally the minoxidil is present in an amount of from about 0.1% to about 20% by total weight of a topical composition. Preferably, the minoxidil is present in an amount of from about 0.5% to about 5% by total weight of a topical composition. The topical composition can be either an aqueous or nonaqueous formulation or wax based formulation.

The method of the present invention can include the additional step of periodically reapplying the minoxidil to the unguis. The reapplication can be done as often as found necessary to achieve growth. Generally, the minoxidil is formulated into a topical composition comprising dimethylacetamide, ethylalcohol, or propylene glycol or combinations thereof.

DETAILED DESCRIPTION OF THE INVENTION

The present invention provides a method for enhancing unguis growth by treating the unguis with a minoxidil containing composition. Specifically, the growth region of the unguis is treated, more preferably, the specialized epithelial cells, matrix or stratum lucidum of the skin.

The active component of the topical treatment is minoxidil which chemically is 6-amino-1,2-dihydro-hydroxy-2-imino-4-piperidinopyrimidine and analogs thereof. The preparation of these compounds are described in U.S. Pat. Nos. 3,382,247, 3,461,461 and 3,644,364 and J. M. McCall, et al., Journal of Organic Chemistry, 40, 3304 (1975) all of which are hereby incorporated by reference. Related compounds are sulfoxypyrimidinium, -pyridinium, and -triazinium which are described in U.S. Pat. No. 4,287,338 herein incorporated by reference. Hereinafter, the term "minoxidil" means any of the various forms of 6-amino-1,2-dihydro-hydroxy-2-imino-4-piperidinopyrimidine, derivatives and analogs thereof.

The composition is a formulation of minoxidil suitable for topical or local administration. The term "topical" means a compound of minoxidil incorporated in a suitable pharmaceutical carrier which can be applied at the growth site of the unguis for local action.

Typical topical compositions include those pharmaceutical forms in which the compound is applied externally by direct contact with the surface to be treated. Conventional pharmaceutical forms for this purpose include ointments, waxes, lotions, pastes, jellies, sprays, aerosols, and the like in aqueous or nonaqueous formulations. The term "ointment" embraces formulations (including creams) having oleaginous, absorption, water-soluble and emulsion-type bases, e.g., petrolatum, lanolin, polyethylene glycols, as well as mixtures of these.

The percentage by weight of minoxidil utilized ranges from about 0.1% to about 20.0% of the pharmaceutical preparation, preferably from about 0.5% to about 5% and in these preparations the aforesaid pharmaceutical carrier for topical application constitutes a major amount of the said preparation.

Preparation of topical compositions are disclosed in U.S. Pat. Nos. 4,139,619 and 4,596,812, both herein incorporated by reference.

Ideally, compositions containing minoxidil are administered by spraying, dabbing or swabbing on the region of the unguis where it emerges from the skin, such as the proximal nail fold in humans. Other less specific methods can be employed provided the active ingredient, minoxidil, is delivered to the growth region of the unguis. Preferably, the minoxidil containing composition is periodically applied to the treatment area on a routine basis to enhance growth of the unguis. In animals it may be necessary to reapply the composition more frequently to compensate for loss due to the animal's activity. In humans the composition can be applied through many sources including fingernail polishes, moistened pads or soaking in dilute solutions.

The subject treatment may be used where brittle nails, hoofs, claws or talons or other disorders are diagnosed. Also, where poor peripheral circulation and onychomycosis are indicated the subject treatment may be used. The treatment may also be used for enhancing the growth of nails, hoofs, claws or talons where greater than normal growth is desired.

We claim:

1. A method for enhancing the growth of unguis in animals including humans comprising:
   topically applying to a region of the unguis where it emerges from the skin an effective amount of minoxidil.

2. The method of claim 1 wherein said minoxidil is present in an amount of from about 0.1% to about 20% by total weight of a topical composition.

3. The method of claim 2 wherein said minoxidil is present in an amount of from about 0.5% to about 5% by total weight of a topical composition.

4. The method of claim 1 wherein said method additionally comprises the periodic reapplication of minoxidil to said region of the unguis.

5. The method of claim 1 wherein said minoxidil is applied in a formulation comprising:
   dimethylacetamide;
   ethylalcohol;
   propylene glycol; or
   combinations thereof.

* * * * *